(12) United States Patent
Kesar

(10) Patent No.: US 12,708,391 B2
(45) Date of Patent: Aug. 18, 2026

(54) ENDOSCOPIC OPEN WIRE SNARE SYSTEM

(71) Applicant: Varun Kesar, Roanoke, VA (US)

(72) Inventor: Varun Kesar, Roanoke, VA (US)

(73) Assignee: Varun Kesar, Roanoke, VA (US)

( * ) Notice: Subject to any disclaimer, the term of this patent is extended or adjusted under 35 U.S.C. 154(b) by 238 days.

(21) Appl. No.: 18/461,644

(22) Filed: Sep. 6, 2023

(65) Prior Publication Data

US 2024/0074774 A1 Mar. 7, 2024

Related U.S. Application Data

(60) Provisional application No. 63/403,892, filed on Sep. 6, 2022.

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC ............ A61B 17/221; A61B 17/32056; A61B 2017/2212; A61B 2017/00358; A61B 2017/2215
See application file for complete search history.

(56) References Cited

U.S. PATENT DOCUMENTS 5,201,741 A 4/1993 Dulebohn
5,486,182 A * 1/1996 Nakao .................... A61B 18/14 606/110
5,522,819 A 6/1996 Graves et al.
5,551,443 A 9/1996 Sepetka et al.
5,632,746 A * 5/1997 Middleman ........ A61B 17/0469 606/174
6,074,378 A 6/2000 Mouri et al.
6,391,018 B1 5/2002 Tanaka et al.
6,500,185 B1 12/2002 Mathews et al.
6,554,842 B2 4/2003 Heuser et al.
6,620,172 B1 9/2003 Dretler et al.
6,652,536 B2 11/2003 Mathews et al.
7,058,456 B2 6/2006 Pierce
7,387,632 B2 * 6/2008 Ouchi .............. A61B 17/32056 606/113

(Continued)

FOREIGN PATENT DOCUMENTS

WO WO-2022063788 A1 * 3/2022 ......... A61B 18/1492

*Primary Examiner* — Tan-Uyen T Ho
*Assistant Examiner* — Osama Nemer
(74) *Attorney, Agent, or Firm* — Davé Law Group, LLC; Raj S. Davé

(57) ABSTRACT

An embodiment relates to a product comprising an open loop polypectomy snare comprising: a) a handle; b) a tubular sheath having proximal and distal ends, the distal end defining a longitudinal axis; c) a snare wire having a first end and a second end extending from cavity of the tubular sheath and relatively movable with respect to the tubular sheath, wherein the first end is attached to the handle, d) at least two snare hemi-loops attached to the second end of the snare wire, wherein the hemi-loops configured to advance and recede inside the tubular sheath such that the hemi-loops are in closed form inside the tubular sheath, and when the hemi-loops advance from the tubular sheath, they open to encircle a matter of choice and join at a joint to form a closed loop to resect the matter of choice.

20 Claims, 4 Drawing Sheets

(56) References Cited

U.S. PATENT DOCUMENTS

| | | | | |
|---|---|---|---|---|
| 9,962,253 | B2 * | 5/2018 | Johnsen | A61F 2/0105 |
| 10,799,261 | B2 | 10/2020 | Nolan et al. | |
| 11,172,915 | B2 * | 11/2021 | Baril | A61B 17/00234 |
| 2002/0068944 | A1 * | 6/2002 | White | A61B 17/221 606/114 |
| 2002/0188304 | A1 * | 12/2002 | Mollenauer | A61B 17/04 606/148 |
| 2003/0220654 | A1 * | 11/2003 | Pineda | A61B 17/32056 606/113 |
| 2006/0189978 | A1 * | 8/2006 | Smith | A61B 18/14 606/47 |
| 2006/0229638 | A1 | 10/2006 | Abrams et al. | |
| 2008/0228209 | A1 | 9/2008 | DeMello et al. | |
| 2009/0209987 | A1 | 8/2009 | Mathews et al. | |
| 2014/0364866 | A1 * | 12/2014 | Dryden | A61B 18/148 606/113 |
| 2015/0105789 | A1 * | 4/2015 | Raybin | A61B 17/32056 606/113 |
| 2017/0007279 | A1 | 1/2017 | Sharma | |
| 2017/0027582 | A1 * | 2/2017 | Khoury | A61B 17/221 |
| 2017/0049471 | A1 * | 2/2017 | Gaffney | A61B 17/32002 |
| 2018/0028219 | A1 * | 2/2018 | Folan | A61B 10/02 |
| 2018/0092661 | A1 * | 4/2018 | Prabhu | A61B 17/3201 |
| 2020/0008926 | A1 | 1/2020 | Power | |
| 2020/0330112 | A1 * | 10/2020 | Verma | A61B 17/221 |

* cited by examiner

ELECTROMAGNETIC JOINT AT HINGE.

ENDOSCOPIC OPEN WIRE SNARE SYSTEM

RELATED APPLICATION

This application claims priority from U.S. provisional application 63/403,892 filed on Sep. 6, 2022, and titled as, "Endoscopic Open Wire Snare System", which is incorporated herein by reference in its entirety.

FIELD OF THE INVENTION

This invention relates to snares, more specifically polypectomy snare, more specifically to an open wire snare system having at least two adjustable hemi-loops that can be closed or open using handle to encircle the lesion.

BACKGROUND OF INVENTION

An endoscopy snare is an endoscopic resection device used to remove lesions in the gastro-intestinal tract commonly referred to as polyps, with the procedure commonly referred to as polypectomy. The device is also used sometimes to remove stents from the biliary tract/pancreatic duct or other foreign body from GI tract.

Snares are often used to capture and retrieve intravascular objects. These objects have a wide range of shapes and sizes. The arteries, veins, or heart chambers in which they are lodged also vary considerably in shape and size, as does the intravascular route that which must be traversed to reach the object.

Currently, the polyps are removed by closed loop snares. Encircling a large polyp is often difficult with existing closed loop snares, as the size of the polyp, particularly pedunculated polyps, inhibits the seating of the snare's loop around the base of the polyp, which in turn prevents the typically necessary step of cauterization used to facilitate removal.

Sessile polyps (i.e., large, flat polyps) often require the creation of a saline pillow beneath the polyp by using a submucosal saline injection technique to separate the tissue from the colon wall to reduce the chance of removal resulting in thermal injury or perforation of the colon wall.

Difficult polyps are often removed piecemeal, sometimes over several procedures. The removal of polyps in this manner increases the risk to the patient, adds to the backlog of procedures scheduled for surgical suites, and unnecessarily consumes the valuable time of the clinician and support staff. Large sessile polyps located in sharp sigmoid bends can also be difficult and require individualized approaches, especially when utilizing conventional closed loop polypectomy snares.

US20140364866A1 relates to "an open loop snare device including a means for securely closing the loop. In some embodiments, a snare device comprises a snare wire and a capture mechanism wherein, when the snare wire is advanced, the snare wire extends from a distal portion of the device along an arcuate path curving back toward the capture mechanism such that, after the snare wire is advanced, activation of the capture mechanism captures the snare wire, creating a formed loop around a target tissue. Retraction of at least one of the snare wire and capture mechanism contracts the formed loop, resecting the target tissue, which is incorporated herein by reference in its entirety.

Other documents that may be of interest may include the following, all of which are incorporated herein by reference: U.S. Pat. No. 7,058,456 B2, inventor Pierce, which issued Jun. 6, 2006; U.S. Pat. No. 6,652,536 B2, inventors Mathews et al., which issued Nov. 25, 2003; U.S. Pat. No. 6,620,172 B1, inventors Dretler et al., which issued Sep. 16, 2003; U.S. Pat. No. 6,554,842 B2, inventors Heuser et al., which issued Apr. 29, 2003; U.S. Pat. No. 6,500,185 B1, inventors Mathews et al., which issued Dec. 31, 2002; U.S. Pat. No. 6,391,018 B1, inventors Tanaka et al., which issued May 21, 2002; U.S. Pat. No. 6,074,378, inventors Mouri et al., which issued Jun. 13, 2000; U.S. Pat. No. 5,551,443, inventors Sepetka et al., which issued Sep. 3, 1996; U.S. Pat. No. 5,522,819, inventors Graves et al., which issued Jun. 4, 1996; U.S. Patent Application Publication No. US 20200008926 A1, inventor Power, which was published Jan. 9, 2020; U.S. Patent Application Publication No. US 20090209987 A1, inventors Mathews et al., which was published Aug. 20, 2009; U.S. Patent Application Publication No. US 20080228209 A1, inventors DeMello et al., which was published Sep. 18, 2008; and U.S. Patent Application Publication No. US 20060229638 A1, inventors Abrams et al., which was published Oct. 12, 2006.

SUMMARY OF INVENTION

An embodiment relates to a product comprising an open loop polypectomy snare comprising: a) a handle; b) a tubular sheath having proximal and distal ends, said distal end defining a longitudinal axis; c) a snare wire having a first end and a second end extending from cavity of the tubular sheath and relatively movable with respect to the tubular sheath, wherein the first end is attached to the handle, d) at least two snare hemi-loops attached to the second end of the snare wire, wherein said hemi-loops configured to advance and recede inside the tubular sheath such that said hemi-loops are in closed form inside the tubular sheath and when said hemi-loops advance from the tubular sheath, they open to encircle a matter of choice and join at a joint to form a closed loop to resect the matter of choice; and wherein movement of said hemi-loops from the tubular sheath and/or opening and closing of said hemi-loops are controlled by the handle; wherein the polypectomy snare is configured for removal of a polyp in endoscopic resection.

In one embodiment, hemi-loops comprise a first hemi-loop and a second hemi-loop, wherein the first hemi-loop and the second hemi-loop are made of the same material. Choice of material may include nitinol or other material.

In one embodiment, hemi-loops comprise a first hemi-loop and a second hemi-loop, wherein the first hemi-loop and the second hemi-loop are made of different material.

In one embodiment, the first hemi-loop is rigid, and the second hemi-loop is flexible.

In one embodiment, the joint of said hemi-loops comprises a hinge joint, a magnet or an electromagnet joint, or a combination thereof.

In one embodiment, the matter of choice comprises a lesion, a polyp, or a foreign body or a combination thereof.

In one embodiment, a portion of the snare wire and at least one of said hemi-loops are electrically conductive and configured to cut the matter of choice in contact with a conductive portion of the hemi-loops when the snare is activated.

In one embodiment, the handle includes means for applying a cautery current to the portion of the snare wire and at least one of the hemi-loops.

In one embodiment, the snare device is a cold snare polypectomy or hot snare polypectomy.

In one embodiment, the snare device as disclosed is configured to resect a polyp having a size in a range of about 0.5 mm, 1 mm, 2 mm, 4 mm, 8 mm, 10 mm, 15 mm, 20 mm, 25 mm, 30 mm, 40 mm, 50 mm, 75 mm, or 100 mm or more.

In one embodiment, width of the snare wire is about 0.05 mm, 0.1 mm, 0.5 mm, 0.75 mm, 1 mm, 2 mm, 4 mm, 8 mm, 10 mm or more.

In one embodiment, width of both the hemi-loops is same. In one embodiment, width of both the hemi-loops is different.

In one embodiment, size of the closed loop formed by the hemi-loops in its closed configuration is in a range of about 1 mm to about 50 mm. The size of the closed loop may be in a range of about 0.5 mm, 1 mm, 2 mm, 4 mm, 8 mm, 10 mm, 15 mm, 20 mm, 25 mm, 30 mm, 40 mm, 50 mm, 75 mm, or 100 mm or more.

In one embodiment, the shape of at least one of the hemi-loops depends on the anatomy of the matter of the choice to be resected. In one embodiment, the hemi-loops wire has memory points so that when the hemi-loops are joined at the hinge joint, the shape of the snare is maintained.

In one embodiment, the length of the hemi-loops can be controlled independently so that the location of the hinge joint may differ.

In one embodiment, at least one of the hemi-loops comprises a monofilament or a braided wire.

In one embodiment, the resecting of the matter of the choice is via a mechanical means and/or by an electrosurgical means.

In one embodiment, the handle comprises a means to open and close the hemi-loops simultaneously or independently.

In one embodiment, the tubular sheath comprises an insulating material, which could be of different types, as construed by a person skilled in the art.

In one embodiment, the insulating material is plastic.

BRIEF DESCRIPTION OF THE FIGURES

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numerals represent like parts.

DETAILED DESCRIPTION

Definitions and General Techniques

Figure 1:
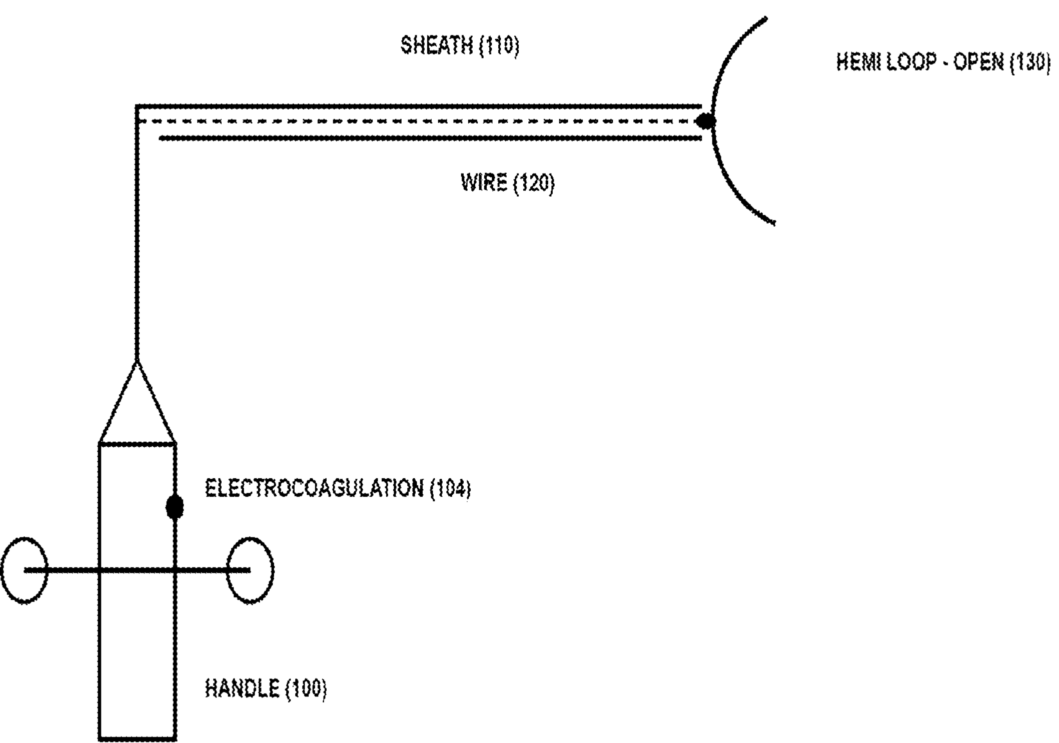
FIG. 1 shows device handle in an open configuration.
Figure 2:
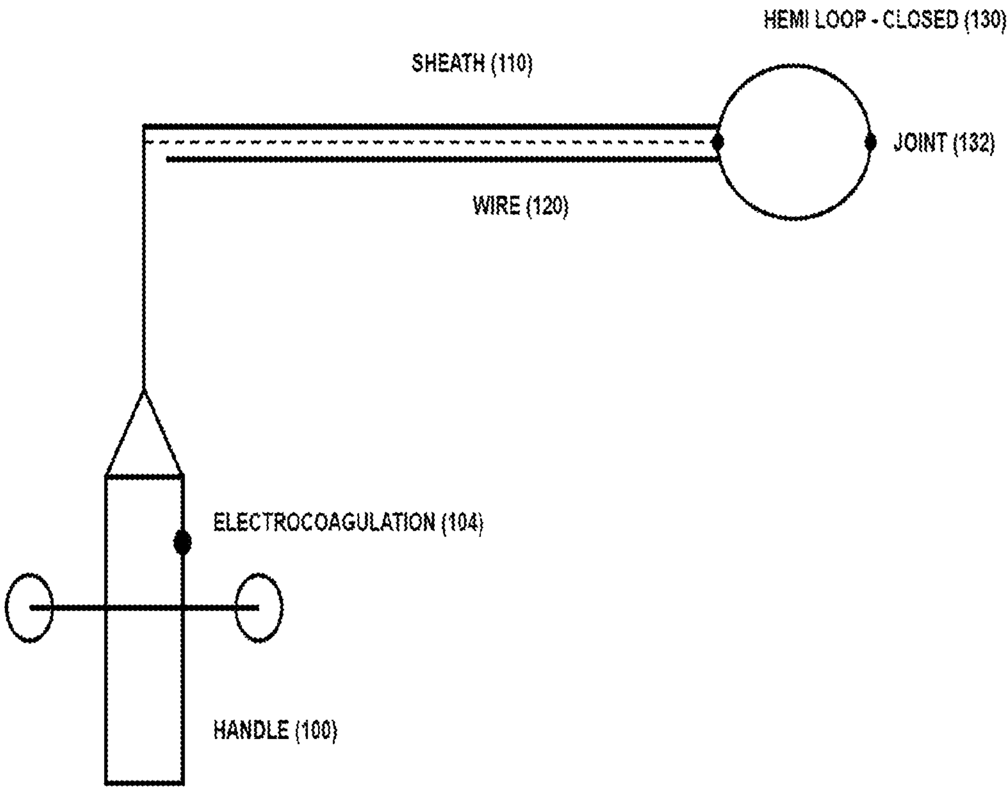
FIG. 2 shows device handle in a closed configuration.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include" and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present invention shall have the meanings that are commonly understood by those of ordinary skill in the art. Further, unless otherwise required by context, singular terms shall include pluralities, and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of, embodiments herein and other related fields described herein are those well-known and commonly used in the art.

The recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The present invention is directed towards multiple embodiments. The following disclosure is provided to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications, and equivalents consistent with the principles and features disclosed. For purposes of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

The following terms and phrases, unless otherwise indicated, shall be understood to have the following meanings.

The term "polypectomy snare" is defined as a snare used for retrieving and/or manipulating an object within a space, such as a body lumen. They are commonly used to remove lesions in the gastrointestinal tract referred as polyps, with procedure commonly referred as polypectomy. The device is also used sometimes to remove stents from the biliary tract/pancreatic duct or other foreign body from the GI tract.

In an embodiment, the polypectomy snare is an open loop polypectomy snare.

Polypectomy snares incorporate a monopolar wire loop (in our case, an open hemi-loop) electrode (if it is hot) that is advanced beyond a plastic insulating catheter/sheath to encircle the target tissue, which is then transected via mechanical and/or electrosurgical cutting as the loop is withdrawn into the catheter. All snares are designed for use with electrocautery, but either hot or cold techniques can be used with any device.

In an embodiment, the open loop polypectomy snare comprises a handle. The handle has open and close functions to change configuration of the wire loop (open/close) to engulf and resect the polyp/lesion/foreign body. In an embodiment, the wire loops in open configuration are in form of hemi-loops. In an embodiment, in the closed configuration, the hemi-loops join together at a joint to form a closed loop.

The term "hemi-loops" includes any shape, configuration, or size of two open loops, that on being joint at a position, are capable to form a closed loop. For example, if the loop is circular, them the hemi-loops could be two semi-circles, or one hemi-loop could be one quadrant of the circle and the other hemi-loop could be the other three quadrants of the circle, or one hemi-loop could be any one portion of the circle and the other hemi-loop could be the rest of the portion of the circle. Similarly, if the closed loop is in triangular form, then the hemi-loops may be in the shape of a seven or the like. The term hemi-loops should not be restricted to two half circles of a loop. A target tissue, such as a polyp, can have any type of shape, such as a round shape or a completely asymmetrical shape. To operate on different types of such target tissues, snare hemi-loops are typically available in various shapes.

In an embodiment, hemi-loops can be closed or open using handle to encircle the lesion. This can be of various sizes depending upon the anatomy of the lesion to be resected. They can be made up of monofilament or braided wires of various gauges and different elements.

In an embodiment, the snare handle may control the movement of the snare wire and its snare hemi-loops relative to the sheath.

In an embodiment, the snare handle may include a number of other structural features, including finger rings, and a plug for connection to a source of cautery current. In an embodiment, the handle may also have an attachment to an electrosurgical unit. Snare wire may be moved by the snare handle any suitable distance, at any suitable speed, and/or with any suitable amount of force.

Snare handle may be configured to remain outside a patient's body during a procedure and may allow a user to control snare hemi-loops, for example, by applying an axially directed pushing or pulling force on the snare wire to extend open snare hemi-loops out of the distal end of the sheath or retract snare hemi-loops into the distal end of the sheath, respectively.

In an embodiment, the snare device further comprises a plurality of one-way valves to allow water or saline solution to flow in one direction only and not leak out of the snare device. In one embodiment, the plurality of valves comprises a first valve positioned at the distal end of the sheath, a second valve positioned at the infusion port, and a third valve positioned at the electrocautery port. The plurality of valves enable a saline solution or water column to be maintained at all times within the sheath, in contact with the snare wire, thereby obviating a need to constantly flush water within the sheath. Additionally, when electrocautery is being performed, it is desirable for the saline solution or water to not escape or leak out of the snare handle and electrocute the user. The intended valve function can be accomplished by valves known in the field, including O-rings to prevent leakage or backflow of water, and can be accomplished with one or more valves as described in US20170007279A1, which is incorporated herein by reference in its entirety.

In an embodiment, extending or advancing snare hemi-loops out of the distal end of the sheath may cause snare hemi-loops to transition from a contracted state to an expanded state. It may further allow the snare hemi-loops to join together to form a closed loop. Likewise, retracting or receding snare hemi-loops into the distal end of sheath may cause the snare close configuration to open and further allow the transition of hemi-loops back from an expanded state to a contracted state.

In an embodiment, the extending snare hemi-loops may only expand from their contracted state, and receding may only contract the hemi-loops back into the sheath.

In an embodiment, expansion/contraction of hemi-loops and open and close configuration of the hemi-loops may be independently controlled by the handle.

Snare handle may also be configured to control the hemi-loops in open and close configuration to engage, grasp, cut, sever, collect, and/or cauterize tissue.

In an embodiment, the hemi-loops can grasp or engage with the matter of choice, such as a polyp, by encircling the polyp from sideways.

In an embodiment, the handle as described in U.S. Ser. No. 10/799,261B2, is incorporated herein by reference in its entirety. In an embodiment, the handle may be as disclosed in US20060189978A1.

In an embodiment, the snare as described herein comprises a tubular sheath.

The term sheath/catheter refers to an insulated covering that covers the wire hemi-loop while it is inside the scope channel in a closed position. This comes in various sizes and lengths depending on the type of endoscope used. The catheter has a lumen through which the wire hemi-loop may be slidably inserted while in its collapsed state. As the wire is moved distally relative to the catheter, the portion of the distal wire hemi-loop that emerges distally beyond the catheter opens from its collapsed state to its expanded state.

In an embodiment, the snare herein comprises a snare wire. The snare wire having a first end and a second end extending from the cavity of the tubular sheath and is relatively movable with respect to the tubular sheath.

In an embodiment, the proximal end of the snare wire is attached to the handle, and the distal end of the snare wire is attached to hemi-loops. In an embodiment, the proximal end of the snare wire may be attached to a cable that further attaches to a handle. In an embodiment, the snare wire may be curved to form hemi-loops. In an embodiment, the hemi-loops may be made of the same material as that of the snare wire. In an embodiment, the hemi-loops and the snare wire are made of different materials. In an embodiment, both hemi-loops may be made of the same material or different material. In an embodiment, one hemi-loop may be flexible and the other may be rigid.

In an embodiment, the snare wire and/or hemi-loops can be any conventional surgical snare wire. It can be a type of metal, (for example, stainless steel), certain types of plastics, or even carbon fiber. Furthermore, certain types of metal materials can be welded together to form a composite wire.

Additionally, it is understood that special types of wires can be used. For example, special shape memory effect wire, for example Nitinol, available from Special Metals, Inc., Middle Settlement Road, New Hartford, N.Y. 13413, could be utilized in a fashion to form even smaller contracted loop ends 32, in turn allowing even smaller diameters for tip 14. This is described in U.S. patent application Ser. No. 07/557,536, filed Jul. 24, 1990, and entitled "Surgical Snare With Shape Memory Effect Wire" which is incorporated by reference herein.

In an embodiment, snare wire and/or hemi-loops may be different stiffness levels across certain ranges of temperatures. In an embodiment, the snare loop has a first stiffness level below 30 degrees Celsius temperature and a second stiffness level above 30 degrees Celsius temperature.

In an embodiment, one or both hemi-loops snare loops are pulled in and out of the sheath to vary the stiffness level of the deployed hemi-loops wire. The hemi-loops are in a first stiffness when in the sheath and in higher stiffness when outside the sheath.

In an embodiment, the closed configuration of hemi-loops is desired to be soft, that is, of the first stiffness, when being placed around a target tissue and needs to be stiffer, that is, of the second stiffness, when the target tissue is constricted (similar to a noose).

The snare wire and/or hemi-loops may be made from a memory shape material such as a memory shape alloy, for example, nickel titanium, also known as nitinol, or a memory shape polymer.

The open loop endoscopic snare device can be rotated within an endoscope's instrument insertion channel from the proximal end of the endoscope to modify the orientation of the snare wire hemi-loops.

In an embodiment, the first hemi-loop incorporates a first magnet on its distal end and the second a magnet or an electromagnet on the distal end of the second hemi-loop to facilitate, or alternatively, to guide the hemi-loop to form a joint that may consequently form a closed loop. In an embodiment, the joint is an electromagnetic joint.

Figure 3:
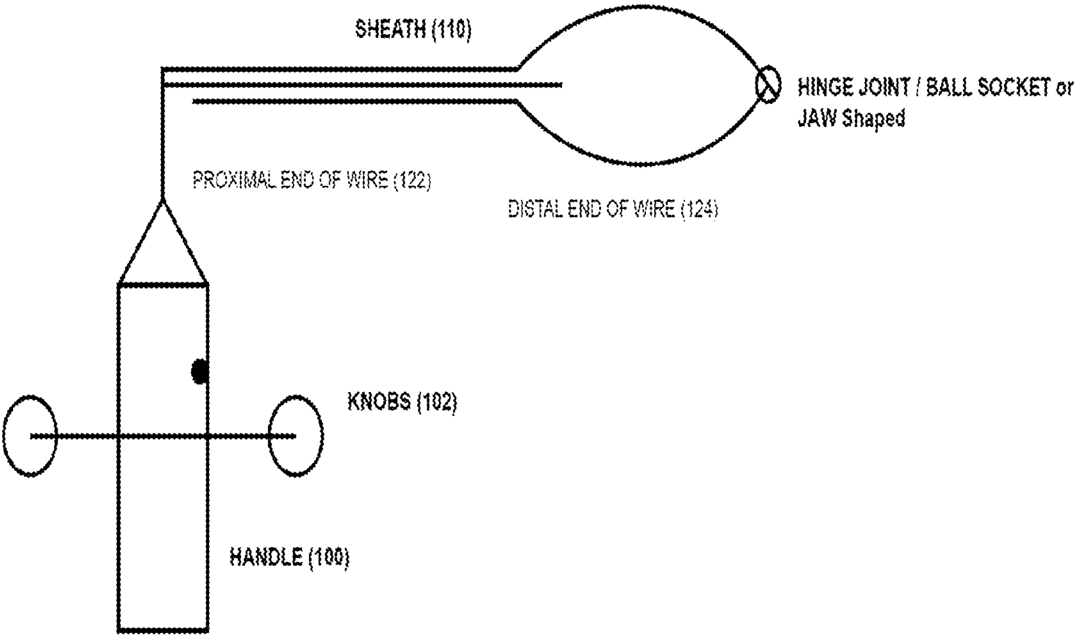
FIG. 3 shows different configurations at the hinge (ball/socket) or jaw shaped.
Figure 4:
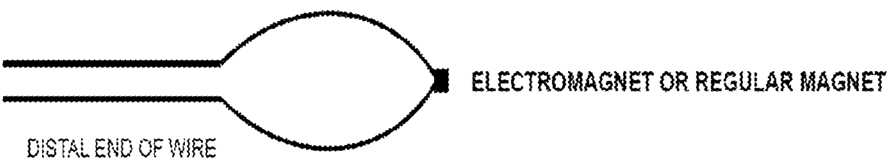
FIG. 4 shows the distal end of the sheath and wire. The hemi-loop are attached using an electromagnet or regular magnet to make a closed loop. The hemi-loop can move simultaneously or independently using the knob located in the handle, allowing variable configuration when they join to perform a closed loop.
Figure 4:
Figure 4:
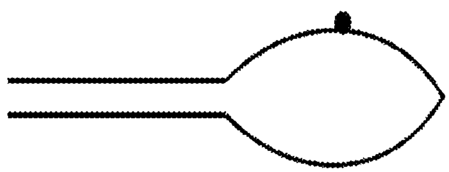

FIG. 3 shows mechanical joints at hinges of various types. Joints could be ball-socket or jaw shaped. In an embodiment, the knob, when pulled up, opens the distal end of the wire into the expanded configuration, allowing the hemi-loops to unite, which forms a closed loop, and circuit can form if electrosurgery is desired. After that, the knob is pulled down to close the snare for performing polypectomy either mechanically or with the help of electrosurgical apparatus.

In an embodiment, the distal ends of the hemi-loops incorporate opposing jaws that may fit together as a lock and key to form a joint. In an embodiment, the distal ends of hemi-loops may have both magnet and opposing jaws to facilitate forming a joint. In an embodiment, the joint is a hinge.

In an embodiment, the distal end of one hemi-loop may be curved to form a first hook, and the distal end of other hemi-loop may be in the form of a second hook that together could form a closed loop.

In an embodiment, upon introduction to the polyp removal site, distal movement of the snare wire relative to the sheath handle causes the snare hemi-loops to extend distally from the sheath and transition from the insertion configuration to an extended state. In the extended state, the hemi-loops are in an open configuration, as shown in FIG. 1. In the initial extended state, snare hemi-loops may be in a single plane of the snare wire. Then, hemi-loops encircle the polyp from its neck.

The handle may then close the hemi-loops to form a closed configuration, forming a snare loop that may sever polyp from the polyp removal site through tightening (mechanical) or electrosurgical cutting, which may be imparted via the snare handle.

In an embodiment, the open loop snare device disclosed herein may also be adapted for use in surgical procedures, such as, for example, laparoscopy, and may be used to resect tissues or removal any foreign object of any type.

It is to be appreciated that the invention can be used in many surgical procedures, for example, urological surgery like bladder removal, tonsil removal, sinus and cancer operations, and the like. It can also be used in a retrieving sense for procedures such as orthoscopic surgery.

Those skilled in the art will recognize, or be able to ascertain, using no more than routine experimentation, numerous equivalents to the specific embodiments described specifically in this disclosure. Such equivalents are intended to be encompassed in the scope of the following claims.

All references, including granted patents and patent application publications, referred to herein are incorporated herein by reference in their entirety.

What is claimed is:

1. A product comprising an open loop polypectomy snare comprising:

a) a handle;

b) a tubular sheath having proximal and distal ends, said distal end defining a longitudinal axis;

c) a snare wire having a first end and a second end extending from a cavity of the tubular sheath and relatively movable with respect to the tubular sheath, wherein the first end is attached to the handle, d) at least two snare hemi-loops attached to the second end of the snare wire, wherein said at least two snare hemi-loops are configured to advance and recede inside the tubular sheath such that said at least two snare hemi-loops are configured to be in a contracted state inside the tubular sheath, when said at least two snare hemi-loops advance from the tubular sheath, they are configured to expand to encircle a matter of choice and join at their distal ends at a joint to form a closed loop configuration to resect the matter of choice; and when said at least two snare hemi-loops retract into the tubular sheath, they are configured to separate at their distal ends to open the closed loop configuration, and the at least two snare hemi-loops contract from its expanded state to the contracted state;

wherein movement of said at least two snare hemi-loops from the tubular sheath and/or opening and closing of said at least two snare hemi-loops are controlled by the handle;

wherein the open loop polypectomy snare is configured to remove the matter of choice in an endoscopic resection;

wherein a portion of the snare wire and at least one of the hemi-loops of said at least two snare hemi-loops comprise an electrically conductive material that on a supply of a cautery current is configured to cut the matter of choice electrically; and wherein said handle comprises a feature configured to supplying the cautery current to the electrically conductive material.

2. The product of claim 1, wherein said at least two snare hemi-loops comprise a first hemi-loop and a second hemi-loop, wherein the first hemi-loop and the second hemi-loop are made of the same material.

3. The product of claim 1, wherein said at least two snare hemi-loops comprise a first hemi-loop and a second hemi-loop, wherein the first hemi-loop and the second hemi-loop are made of different material.

4. The product of claim 3, wherein the first hemi-loop is more rigid relative to the second hemi-loop.

5. The product of claim 1, wherein the joint of said at least two snare hemi-loops comprises a hinge joint, a magnet, an electromagnet joint or a combination thereof.

6. The product of claim 1, wherein the matter of choice comprises a lesion, a polyp or a foreign body or a combination thereof.

7. The product of claim 1, wherein said snare is a cold snare polypectomy or a hot snare polypectomy.

8. The product of claim 6, wherein a size of the polyp is in a range of about 1 mm to about 50 mm.

9. The product of claim 1, wherein a width of the snare wire is about 0.1 mm to 1 mm.

10. The product of claim 2, wherein a width of both the hemi-loops is same.

11. The product of claim 2, wherein a width of both the hemi-loops is different.

12. The product of claim 1, wherein a size of the closed loop formed by the at least two snare hemi-loops is in a range of about 1 mm to about 50 mm.

13. The product of claim 1, wherein a shape of at least one of the hemi-loops of said at least two snare hemi-loops depends on anatomy of the matter of the choice to be resected.

14. The product of claim 1, wherein at least one of the hemi-loops of said at least two snare hemi-loops comprises a monofilament or a braided wire.

15. The product of claim 1, wherein the handle comprises a knob configured to open and close the at least two snare hemi-loops either simultaneously or independently to achieve different configurations.

16. The product of claim 1, wherein the tubular sheath comprises an insulating material.

17. The product of claim 16, wherein the insulating material comprises plastic.

18. The product of claim 1, wherein at least one of the hemi-loops of said at least two snare hemi-loops comprises a memory material.

19. A product comprising an open loop polypectomy snare comprising:

a) a handle;

b) a tubular sheath having proximal and distal ends, said distal end defining a longitudinal axis;

c) a snare wire having a first end and a second end extending from a cavity of the tubular sheath and relatively movable with respect to the tubular sheath, wherein the first end is attached to the handle, d) at least two snare hemi-loops attached to the second end of the snare wire, wherein said at least two snare hemi-loops are configured to advance and recede inside the tubular sheath such that said at least two snare hemi-loops are configured to be in a contracted state inside the tubular sheath, when said at least two snare hemi-loops advance from the tubular sheath, they are configured to expand to encircle a matter of choice and join at their distal ends at a joint to form a closed loop configuration to resect the matter of choice; and when said at least two snare hemi-loops retract into the tubular sheath, they are configured to separate at their distal ends to open the closed loop configuration and the at least two snare hemi-loops contract from its expanded state to the contracted state;

wherein movement of said at least two snare hemi-loops from the tubular sheath and/or opening and closing of said at least two snare hemi-loops are controlled by the handle; and wherein the open loop polypectomy snare is configured to remove the matter of choice in an endoscopic resection.

20. The product of claim 19, wherein the snare wire and at least one of the hemi-loops of said at least two snare hemi-loops are retractable into the tubular sheath and configured to apply mechanical force to resect the matter of choice mechanically.

* * * * *